United States Patent
Ngai et al.

(10) Patent No.: US 8,023,110 B1
(45) Date of Patent: Sep. 20, 2011

(54) PRIORI CRACK DETECTION IN SOLAR PHOTOVOLTAIC WAFERS BY DETECTING BENDING AT EDGES OF WAFERS

(75) Inventors: Samuel Ngai, San Francisco, CA (US); Ady Levy, Sunnyvale, CA (US)

(73) Assignee: KLA-Tencor Corporation, San Jose, CA (US)

( * ) Notice: Subject to any disclaimer, the term of this patent is extended or adjusted under 35 U.S.C. 154(b) by 624 days.

(21) Appl. No.: 12/027,914

(22) Filed: Feb. 7, 2008

Related U.S. Application Data

(60) Provisional application No. 60/888,747, filed on Feb. 7, 2007.

(51) Int. Cl.
*G01N 21/00* (2006.01)

(52) U.S. Cl. .................. 356/237.1; 356/237.2

(58) Field of Classification Search ..... 356/237.1–237.5
See application file for complete search history.

(56) References Cited

U.S. PATENT DOCUMENTS

| | | | | |
|---|---|---|---|---|
| 3,630,627 A | * | 12/1971 | Low et al. | 356/222 |
| 3,877,814 A | * | 4/1975 | Hess et al. | 356/613 |
| 4,837,449 A | * | 6/1989 | Maltby, Jr. | 250/559.11 |
| 5,210,592 A | * | 5/1993 | Bretschneider | 356/613 |
| 5,251,010 A | * | 10/1993 | Maltby, Jr. | 356/613 |
| 5,367,174 A | * | 11/1994 | Bazile et al. | 250/559.45 |
| 6,909,502 B2 | * | 6/2005 | Capaldo et al. | 356/239.2 |
| 2004/0057046 A1 | * | 3/2004 | Abbott et al. | 356/239.1 |
| 2008/0239315 A1 | * | 10/2008 | Borden | 356/364 |

OTHER PUBLICATIONS

U.S. Appl. No. 60/888,747, filed Feb. 7, 2007.

* cited by examiner

*Primary Examiner* — Michael P Stafira
(74) *Attorney, Agent, or Firm* — Joshua D. Isenberg; JDI Patent

(57) ABSTRACT

Methods and systems for determining the quality of a substrate are disclosed. One or more substrates may be examined to determine whether bending is present at the edge of a substrate. The substrate may be accepted if it is determined that bending is not present at the edge of the substrate. The substrate may be rejected if it is determined that bending is present at the edge of the substrate.

45 Claims, 2 Drawing Sheets

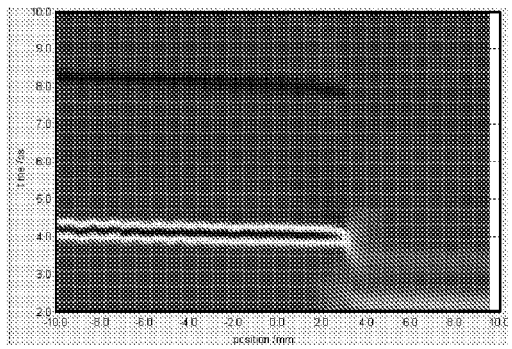
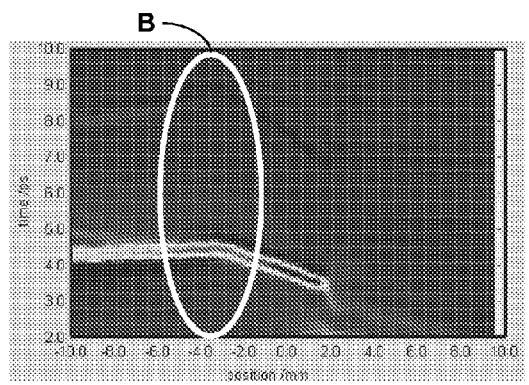
FIG. 5A  FIG. 5B
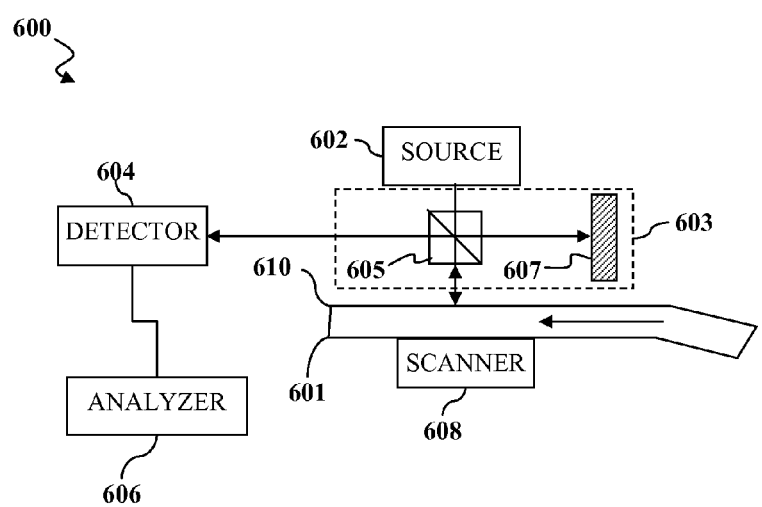
FIG. 6

PRIORI CRACK DETECTION IN SOLAR PHOTOVOLTAIC WAFERS BY DETECTING BENDING AT EDGES OF WAFERS

CROSS-REFERENCE TO A RELATED APPLICATION

This application claims priority from co-pending provisional patent application Ser. No. 60/888,747, which was filed on Feb. 7, 2007, the entire disclosures of which are incorporated herein by reference.

FIELD OF THE INVENTION

This invention generally relates to detection of the cracks in the solar photovoltaic wafers and more particularly to detection of the cracks using imaging techniques.

BACKGROUND OF THE INVENTION

Roughly 95% of solar cells are manufactured using silicon as a substrate. The need to produce more electric power per kilogram of silicon in periods of poly silicon shortage has lead to rigid thickness reductions for single crystal and polycrystalline silicon wafers. Silicon wafers used in solar cell manufacture are often very thin, e.g., only about 250 microns thick. The mechanical strength of single crystal and polycrystalline silicon wafers and cells is strongly dependent on the length and the position of micro cracks in the silicon wafer material. Micro cracks increase the breakage risk over the whole value chain from the wafer to the finished module, because the wafer or cells is exposed to tensile stress during handling and processing. The use of larger and thinner crystalline silicon wafer increases the risk of yield loss.

About 5% to 10% of solar cell wafers break during manufacturing. Wafer breakage during processing is a very high cost issue. This is particularly true when wafers fail during one of the print steps, general resulting in several minutes of downtime while the operator cleans up the scattered parts and the wet paste. This is also a source of potential contamination. It is believed that wafers frequently fail at the print steps because they come into the process already cracked and the crack then fails when it is stressed during the process step. Wafer cracks can also cause electrical failure during cell or module testing.

Some techniques have been used for detection of microcracks of silicon wafer. Laser-based ultrasound technique is based on using a short laser pulse directed at the wafer to cause a sudden rise in temperature of the wafer material. The temperature rise initiates a sudden but minor expansion of the silicon. The acoustic energy released from the expansion can be used to distinguish between elastic or plastic expansion. The strain energy emitted from the cracks will produce acoustic waves having frequencies characteristic of plastic deformation.

Another technique is Scanning Acoustic Microscopy (SAM). In SAM, a focused acoustic beam is scanned over the front and back surface of the wafers. The sound pulses are transmitted through the wafer and the reflection from the wafer interface is monitored. The ultrasonic pulses are generated by high-frequency piezoelectric transducer. Electrical pulse from high voltage transmitter is converted to mechanical energy. This activation causes the transducer to vibrate at a specific frequency causing ultrasonic pulses to be transmitted from the transducer. These pulses travel through the material at the material velocity and are reflected at the interfaces of the material it strikes. The ultrasonic energy does not travel well through air so the wafers have to be placed in a coupling medium (e.g., a deionized water bath). However, each SAM wafer measurement may take as long as 20 minutes for sample set up and data collection. This is too slow for an inline production process.

There are optical techniques available to detect large and obvious cracks on surface of wafers after the wafers enter the manufacturing line. Examples of such systems include those made by ICOS Vision Systems of Heverlee, Belgium. These systems are based on cameras that collect an image of a solar cell wafer and analyze the image to detect a variety of defects including large surface cracks. Unfortunately, cracks are not always visible to cameras for several reasons. In some cases, the cracks might be sub surface cracks that are not visible to the camera. In other cases the cracks are generated during processing steps such as thermal processes.

To the inventors' best knowledge, there is no commercial inspection technique that images cross-sections of the wafers and screens out cracked wafers or wafers that are liable to crack before they enter the manufacturing line.

It is within this context that embodiments of the present invention arise.

BRIEF DESCRIPTION OF THE DRAWINGS

Other objects and advantages of the invention will become apparent upon reading the following detailed description and upon reference to the accompanying drawings in which:

FIG. 5A is a cross-sectional image of a normal solar cell substrate obtained using terahertz imaging.

FIG. 5B is a cross-sectional image of a cracked solar cell substrate obtained using terahertz imaging.

FIG. 6 is a schematic diagram illustrating an interferometric technique for detecting edge bending.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

The inventors have determined that certain substrates, such as solar cell wafers, exhibit a characteristic bending at an edge of the substrate if the substrate is cracked and no such bending if the substrate is not cracked. The inventors have also determined that in cracked wafers bending is only observable in a relatively narrow region at the edge of the wafer, e.g., within about 10 mm from the edge. If bending is observed in this region, it may be inferred that the bending extends all the way across the wafer even if signs of bending are not observed elsewhere on the wafer. It is noted that features that look like cracks may be observed in solar cell wafers using various imaging techniques. However, these features can appear in both cracked and non-cracked wafers.

Figure 1:
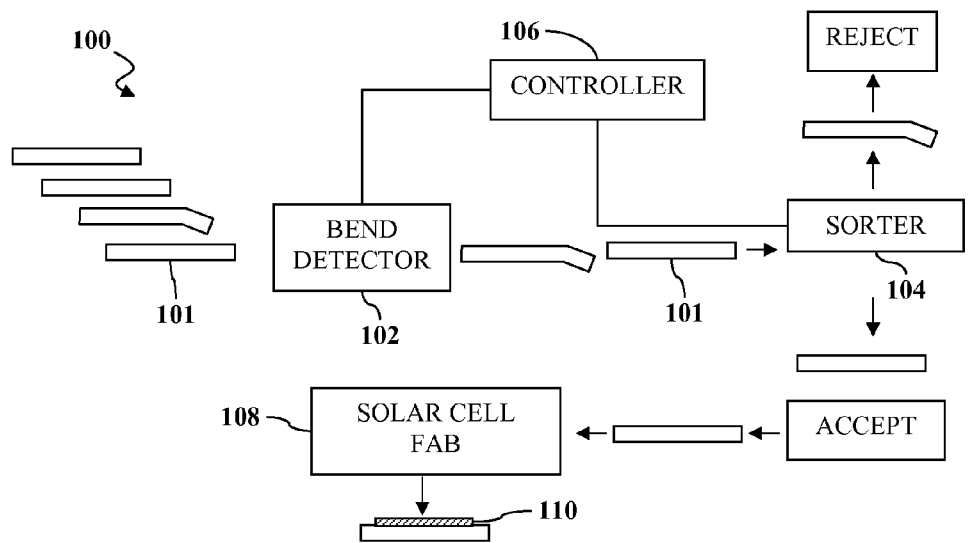
FIG. 1 is a schematic diagram illustrating a substrate quality system and method utilizing detection of edge bending according to embodiment of the present invention.

FIG. 1 illustrates schematically a method and system 100 for determining the quality of a substrate based on the results of the foregoing discussion. The system 100 generally includes a bend detector 102 and a sorter 104. The bend detector 102 is configured to determine whether bending is present at an edge of a substrate 101. The bend detector 102 may use any suitable technique for detecting bending at the edges of the substrates 101. Such techniques may be based on electrical measurements, optical measurements, probing the substrates with radiation or measuring strain in the substrates.

The sorter is configured to accept the substrate 101 if the bend detector 102 determines that bending is not present at the edge of the substrate or reject the substrate 101 if the bend detector 102 determines that bending is present at the edge of the substrate. By way of example, the sorter 102 may include a mechanism that steers accepted substrates to a processing line and steers rejected substrates to a reject bin. The bend detector 102 and sorter 104 may be coupled to a controller 106 and operate in response to instructions from the controller 106. The controller 106 may be a general purpose computer programmed to act as a special purpose computer. Alternatively, the controller 106 may include an application-specific integrated circuit (ASIC).

By way of example, and without loss of generality, the substrates 101 may be solar cell wafers, which may be made of a semiconducting material, such as silicon. Accepted wafers proceed to a solar cell fabrication facility 108, where solar cells 110 may be formed on the wafers by well-known solar cell fabrication processes. Acceptance or rejection of a solar cell wafer may take place after manufacturing the solar cell wafer but before completion of fabrication of one or more solar cells from the wafer. As used herein, manufacturing a solar cell wafer refers to the process of preparing the wafers from raw material. Such a process may include formation of a raw silicon block, sawing the raw block into a finished block having a desired shape, sawing the finished block into individual wafers and polishing one or more surfaces of the wafers. Such wafers are commonly rectangular in shape roughly 156 mm in length by 156 mm in width and about 250 microns thick. Manufacturing the solar cell wafers may take place at a separate facility that is separate from the solar cell fabrication facility 108. As used herein fabrication of solar cells refers to a process of turning a wafer into a solar cell. Such a process may include forming layers of material on the wafer that make up a solar cell.

Preferably, accepting or rejecting the substrate takes place before fabrication of one or more solar cells on the solar cell wafer. The bend detector 102 and sorter 104 may be located at the beginning, middle, or end of processing line at the solar cell fabrication facility 108.

Alternatively, the bend detector 102 and sorter 104 may be located at the end of a solar cell wafer manufacturing line. In a preferred embodiment, the bend detector 102 may be placed for the first unit operation in the solar cell manufacturing line 108 (often the first unit operation is wafer texturing). This can be achieved by carrying the wafers on a conveyer belt and installing the bend detector 102 above and/or below the belt.

Figure 2:
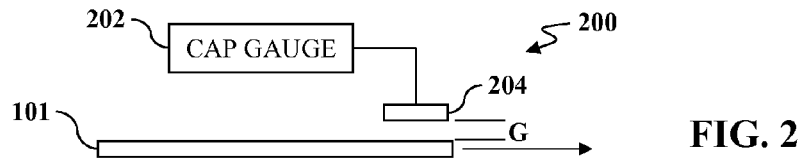
FIG. 2 is a schematic diagram illustrating a substrate quality system and method utilizing capacitive detection of edge bending according to an embodiment of the present invention.

By way of example, a bend detector 200 may include a capacitive gauge 202 having an electrode 204 located proximate the edges of the substrates 101 as shown in FIG. 2. The electrode 204 may move with respect to the edge of the substrate, either by keeping the electrode stationary while the substrates move past it on a conveyer belt or by moving the electrode relative to the substrates 101 or some combination of both. The capacitive gauge 202 may produce an electrical signal that depends on a gap G between the electrode 204 and the edge of a substrate 101. Variations in the electrical signal may indicate a bend at the edge of the substrate.

Figures 3, 4:
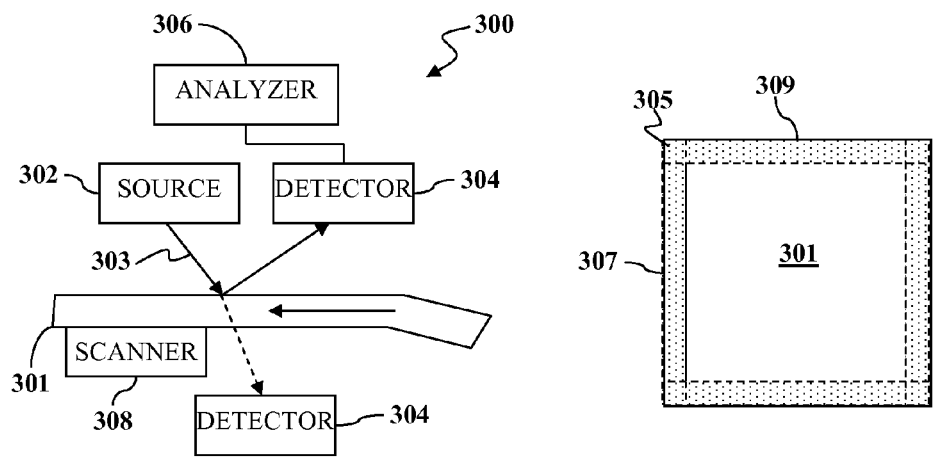
FIG. 3 is a schematic diagram illustrating a substrate quality system and method utilizing optical detection of edge bending according to an embodiment of the present invention.
FIG. 4 is a plan view schematic diagram illustrating locations for obtaining cross-sectional edge images on a substrate according to an embodiment of the present invention.

In an alternative embodiment, the bend detector may implement optical detection of bending at the edges of the substrates. FIG. 3 schematically illustrates an example of a method and system for optical detection of edge bending. As shown in FIG. 3, a bend detector 300 may include a radiation source 302 and a detector 304. The radiation source 302 may be configured to direct incident radiation 303 toward a surface of a substrate 301 at a location proximate an edge of the substrate 301. The detector 304 may be configured to measure a portion of the incident radiation that has been reflected, scattered or transmitted by the location proximate the edge of the substrate. Two or more detectors may be used in some embodiments.

An analyzer 306 may be coupled to the detector 304. The analyzer 306 may be configured to determine whether bending is present at the edge of the substrate 301 from measurements obtained by the detector 304. In a preferred embodiment, the analyzer 306 may include an imaging system configured to generate one or more cross-sectional images of the edge of the substrate. An image analyzer may be used in conjunction with the imaging system. The image analyzer may be configured to analyze the one or more cross-sectional images to determine the presence of bending. The image analyzer may be implemented in hardware, software or some combination of hardware and software.

By way of example, the incident radiation 303 may include radiation in the terahertz, visible, infrared (IR), ultraviolet (UV) or X-Ray regions of the electromagnetic spectrum. The boundaries between different regions of the electromagnetic spectrum are somewhat arbitrary and may differ depending on the field of study. Furthermore, there may be some degree of overlap between different regions. The following discussion is meant to provide some guidelines, but is not definitive. As used herein infrared radiation generally refers to electromagnetic radiation having frequencies ranging from about 3 terahertz ($3 \times 10^{12}$ Hz) and about 300 terahertz ($3 \times 10^{14}$ Hz) corresponding to vacuum wavelengths between about 100 microns and about 1 micron. As used herein, visible radiation generally refers to electromagnetic radiation having frequencies corresponding to vacuum wavelengths of about 800 nanometers to about 400 nanometers. As used herein, ultraviolet radiation generally refers to electromagnetic radiation having frequencies between about $7.5 \times 10^{14}$ Hz and about $3 \times 10^{16}$ Hz corresponding to vacuum wavelengths of about 400 nanometers to about 10 nanometers. The term X-rays, as used herein, generally refers to electromagnetic radiation having frequencies between about $3 \times 10^{16}$ Hz and about $3 \times 10^{19}$ Hz corresponding to vacuum wavelengths of about 10 nanometers to about 10 picometers ($10 \times 10^{-12}$ meters).

As used herein terahertz radiation generally refers to electromagnetic radiation having frequencies between the microwave and infrared regions. Microwave generally refers to electromagnetic radiation with frequencies between about 300 MHz ($3 \times 10^8$ Hz) and about 300 GHz ($3 \times 10^{11}$ Hz). Terahertz radiation is also sometimes known as terahertz waves, terahertz light, T-rays, T-light, T-lux and THz. Terahertz radiation generally falls in a region of the electromagnetic spectrum between about 300 gigahertz ($3 \times 10^{11}$ Hz) and about 3 terahertz ($3 \times 10^{12}$ Hz), corresponding to a range of vacuum wavelength between submillimeter (<1 millimeter) and about 100 microns (roughly corresponding to the longer wavelengths of infrared light).

As illustrated in FIG. 4, the imaging system may be configured to perform a measurement at a location proximate a corner region 305 of the substrate 301 where a first edge region 307 and a second edge region 309 of the substrate intersect. The imaging system may generate a first cross-sectional image corresponding to the first edge and a second cross-sectional image corresponding to the second edge based on measurements taken using radiation incident at the corner 305.

Cross-sectional images may be generated by detecting of terahertz waves reflected from different depths within the wafer allows. Until recently bright sources of radiation and sensitive means of detection of radiation in this range did not exist. Recently, systems have been developed that provide both radiation sources and sensitive detectors that allow imaging using radiation in this range. Examples of commercially-available terahertz imaging systems include TPI™ imaga 1000 and TPI™ imaga 2000 imaging systems from TeraView Limited of Cambridge, United Kingdom. TPI™ is a trademark of TeraView Limited of Cambridge, United Kingdom.

FIGS. 5A-5B illustrate examples of cross-sectional images of cracked and uncracked wafers taken using an imaging system based on terahertz incident radiation. As may be seen by comparing the two images, the uncracked wafer in FIG. 5A exhibits a relatively even pattern of layering. In this particular example, the wafers were about 200 microns thick. The cracked wafer in FIG. 5B, by contrast exhibits a pronounced bending at the location marked B. Such bending features may be identified, e.g., where the analyzer 306 includes a general purpose computer programmed to run appropriately configured image analysis software.

With a terahertz imaging system cross-sectional images of the edges of solar cell wafers may be obtained and analyzed rapidly.

In another embodiment, the radiation source 302 may include a laser configured to direct a laser beam toward a surface of the substrate 301 at a location proximate an edge of the substrate. The bend detector 300 may further include a scanner 308 adapted to scan the laser beam relative to the edge of the substrate 301. Such a scanner may operate by moving the substrate relative to the laser, the laser relative to the substrate or some combination of both. The bend detector may further include a detector configured to measure a deflection of the laser beam by the location proximate the edge of the substrate and an analyzer configured determine whether bending is present from a shift in the deflection of the laser beam. The detector may include a position sensitive detector that produces a signal that depends on a position of the laser beam.

In another alternative embodiment, illustrated in FIG. 6, a bend detector 600 may include a radiation source 602 and an interferometer 603 optically coupled to a substrate 601 and a detector 604. The interferometer 603 is configured to generate an interference pattern using the portion of the incident radiation that has been reflected, scattered or transmitted by a location proximate the edge of the substrate. The interference pattern can be very sensitive to variations in the shape of the substrate. Particular characteristics of interference patterns corresponding to bent and unbent substrates may be determined by observing interference patterns associated with known bent and unbent substrates. Bending of unknown substrates may be determined by monitoring their interference patterns for the characteristics associated with bending. An analyzer 606 may be coupled to the detector for this purpose. A scanner 608 may move the edge of the substrate 601 relative to the interferometer 603 to facilitate scanning of an entire edge of the substrate. By way of example, the interferometer 603 may be a Michelson-type interferometer having a beam splitter 605 and a reference mirror 607. A surface 610 of the substrate 601 provides a sample mirror. Alternative embodiments may use other types of interferometers such as Linnik-type, Fabry-Perot, Mach-Zehnder or differential interferometers. In some embodiments, the interferometer 603 may generate an interference pattern that is affected by transmission of radiation through the substrate 601. For example, the interferometer 603 may be a Fabry-Perot interferometer with the substrate passing between two parallel partially reflecting surfaces. Alternatively, the substrate may pass through a measurement arm of a Mach-Zehnder interferometer.

Embodiments of the present invention provide a relatively rapid, simple and reliable means of determining the presence of cracks in substrates before they are processed. This allows a greater degree of quality control of the substrates and a higher yield of acceptable devices produced using the substrates. In particular, solar cells may be more reliably and less expensively fabricated if cracked wafers can be rejected before solar cells are fabricated on them.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for determining the quality of a substrate, comprising:
   determining whether bending is present within about 10 mm from the edge of the substrate; and
   accepting the substrate if it is determined that bending is not present at the edge of the substrate;
   or rejecting the substrate if it is determined that bending is present within about 10 mm from the edge of the substrate, even if signs of bending are not observed elsewhere on the substrate.

2. The method of claim 1 wherein the substrate is a solar cell wafer.

3. The method of claim 2 wherein accepting or rejecting the substrate takes place before fabrication of one or more solar cells on the solar cell wafer.

4. The method of claim 1 wherein determining whether bending is present includes moving an electrode with respect to the edge and determining the present of bending based on a signal from a capacitive gauge coupled to the electrode.

5. The method of claim 1, wherein determining whether bending is present includes generating one or more cross-sectional images of the location proximate the edge of the substrate.

6. The method of claim 5, wherein determining whether bending is present includes analyzing the one or more cross-sectional images to determine the presence of bending.

7. The method of claim 5 wherein generating the one or more cross-sectional images includes performing a measurement at a location proximate a corner of the substrate where a first and second edge of the substrate intersect, and generating a first cross-sectional image corresponding to the first edge and a second cross-sectional image corresponding to the second edge.

8. The method of claim 5 wherein generating the one or more cross-sectional images includes:
   a) directing incident radiation toward a surface of the substrate at a location proximate an edge of the substrate;
   b) measuring a portion of the incident radiation that has been reflected, scattered or transmitted by the location proximate the edge of the substrate.

9. The method of claim 8 wherein the incident radiation includes radiation in the terahertz THZ, visible, IR, NIR, UV or X-Ray portions of the electromagnetic spectrum.

10. The method of claim 1 determining whether bending is present includes:
   directing a laser beam toward a surface of the substrate at a location proximate an edge of the substrate;
   scanning the laser beam relative to the edge of the substrate;
   measuring a deflection of the laser beam by the location proximate the edge of the substrate; and
   determining whether bending is present from a shift in the deflection.

11. A method for determining the quality of a substrate, comprising:
   directing incident radiation toward a surface of the substrate at a location proximate an edge of the substrate;
   b) measuring a portion of the incident radiation that has been reflected, scattered or transmitted by the location proximate the edge of the substrate;
   c) determining from measurements obtained in b) whether bending is present within about 10 mm from the edge of the substrate; and
   d) rejecting the substrate if it is determined that bending is present within about 10 mm from the edge of the substrate, even if signs of bending are not observed elsewhere on the substrate.

12. The method of claim 11, further comprising accepting the substrate if it is determined that bending is not present.

13. The method of claim 11 wherein the substrate is a solar cell wafer.

14. The method of claim 13 wherein a), b) and c) take place after manufacturing the solar cell wafer but before completion of fabrication of one or more solar cells on the solar cell wafer.

15. The method of claim 11, wherein c) includes generating one or more cross-sectional images of the location proximate the edge of the substrate from the measurements obtained in b).

16. The method of claim 15 wherein c) further includes analyzing the one or more cross-sectional images to determine the presence of bending.

17. The method of claim 15 wherein the location proximate the edge of the substrate is a location proximate a corner of the substrate where a first and second edge regions of the substrate intersect, and wherein c) includes generating a first cross-sectional image corresponding to the first edge region and a second cross-sectional image corresponding to the second edge region.

18. The method of claim 15 wherein the incident radiation is in the terahertz (THZ) range of the electromagnetic spectrum.

19. The method of claim 11 wherein the incident radiation includes radiation in the terahertz THZ, IR, visible, UV or X-Ray portions of the electromagnetic spectrum.

20. The method of claim 11 wherein the incident radiation includes a laser beam.

21. The method of claim 11 wherein b) includes measuring a position of a portion of the laser beam that has been reflected from the location proximate the edge of the substrate.

22. The method of claim 20 wherein a) includes scanning the laser beam along the edge of the substrate, wherein b) includes detecting a shift in deflection of the laser beam; and wherein c) includes determining whether bending is present from the shift in deflection of the laser beam.

23. The method of claim 11 wherein measuring the portion of the incident radiation that has been reflected, scattered or transmitted by the location proximate the edge of the substrate includes generating an interference pattern using the portion of the incident radiation that has been reflected, scattered or transmitted by the location proximate the edge of the substrate.

24. A system for determining the quality of a substrate, comprising:
   a bend detector configured to determine whether bending is present within about 10 mm from an edge of the substrate; and
   a sorter configured to accept the substrate if the bend detector determines that bending is not present within about 10 mm from the edge of the substrate; or reject the substrate if the bend detector determines that bending is present within about 10 mm from the edge of the substrate, even if signs of bending are not observed elsewhere on the substrate.

25. The system of claim 24 wherein the bend detector is located at the beginning of a solar cell fabrication line.

26. The system of claim 24 wherein the bend detector is located in the middle of a solar cell fabrication line.

27. The system of claim 24 wherein the bend detector is located at the end of a solar cell fabrication line.

28. The system of claim 24 wherein the bend detector includes a capacitive gauge configured to move with respect to the edge of the substrate.

29. The system of claim 24 wherein the bend detector includes an imaging system configured to generate one or more cross-sectional images of the location proximate the edge of the substrate.

30. The system of claim 29 further comprising an image analyzer configured to analyze the one or more cross-sectional images to determine the presence of bending.

31. The system of claim 29 wherein the imaging system is configured to perform a measurement at a location proximate a corner of the substrate where first and second edge regions of the substrate intersect, and generating a first cross-sectional image corresponding to the first edge region and a second cross-sectional image corresponding to the second edge region.

32. The system of claim 29 wherein the imaging system includes:
   a) a radiation source configured to direct incident radiation toward a surface of the substrate at a location proximate an edge of the substrate; and
   b) a detector configured to measure a portion of the incident radiation that has been reflected, scattered or transmitted by the location proximate the edge of the substrate.

33. The system of claim 32 wherein the incident radiation includes radiation in the terahertz THZ, visible IR, NIR, or X-Ray portions of the electromagnetic spectrum.

34. The system of claim 32, further comprising an interferometer optically coupled to the substrate and the detector, wherein the interferometer is configured to generate an interference pattern using the portion of the incident radiation that has been reflected, scattered or transmitted by the location proximate the edge of the substrate.

35. The system of claim 34 wherein the bend detector includes:
   a laser configured to direct a laser beam toward a surface of the substrate at a location proximate an edge of the substrate;
   a scanner adapted to scan the laser beam relative to the edge of the substrate;
   a detector configured to measure a deflection of the laser beam by the location proximate the edge of the substrate; and
   an analyzer configured determine whether bending is present from a shift in the deflection of the laser beam.

36. A system for determining the quality of a substrate, comprising:
   a) a radiation source configured to direct incident radiation toward a surface of the substrate at a location proximate an edge of the substrate;
   b) a detector configured to measure a portion of the incident radiation that has been reflected, scattered or transmitted by the location proximate the edge of the substrate;
   c) an analyzer configured to determine from measurements obtained by the detector whether bending is present within about 10 mm from the edge of the substrate; and
   d) a sorter configured to reject the substrate if the analyzer determines that bending is present within about 10 mm from the edge of the substrate, even if signs of bending are not observed elsewhere on the substrate.

37. The system of claim 36, wherein the analyzer is configured to generate one or more cross-sectional images of the location proximate the edge of the substrate from the measurements by the detector.

38. The system of claim 37 wherein the analyzer is further configured to analyze the one or more cross-sectional images to determine the presence of bending at the edge of the substrate.

39. The system of claim 37 wherein the location proximate the edge of the substrate is a location proximate a corner of the substrate where first and second edge regions of the substrate intersect, and wherein the analyzer is configured to generate a first cross-sectional image corresponding to the first edge region and a second cross-sectional image corresponding to the second edge region.

40. The system of claim 37 wherein the incident radiation is in the terahertz (THZ) range of the electromagnetic spectrum.

41. The system of claim 36 wherein the incident radiation includes radiation in the terahertz (THZ), infrared (IR), visible, ultraviolet (UV), or X-Ray portions of the electromagnetic spectrum.

42. The system of claim 36 wherein radiation source includes a laser and the incident radiation is a laser beam from the laser.

43. The system of claim 42 wherein the detector is configured to measure a position of a portion of the laser beam that has been reflected from the location proximate the edge of the substrate.

44. The system of claim 42 further comprising a scanner configured to scan the laser beam along the edge of the substrate, wherein the detector is configured to detect a shift in deflection of the laser beam; and wherein the analyzer is configured to determining whether bending is present from the shift in deflection of the laser beam.

45. The system of claim 36, further comprising an interferometer optically coupled to the substrate and the detector, wherein the interferometer is configured to generate an interference pattern using the portion of the incident radiation that has been reflected, scattered or transmitted by the location proximate the edge of the substrate.

* * * * *